(12) United States Patent
Truckai et al.

(10) Patent No.: US 7,517,349 B2
(45) Date of Patent: Apr. 14, 2009

(54) ELECTROSURGICAL INSTRUMENT AND METHOD

(75) Inventors: Csaba Truckai, Saratoga, CA (US); John H. Shadduck, Menlo Park, CA (US)

(73) Assignee: VNUS Medical Technologies, Inc., San Jose, CA (US)

( * ) Notice: Subject to any disclaimer, the term of this patent is extended or adjusted under 35 U.S.C. 154(b) by 70 days.

(21) Appl. No.: 11/199,555

(22) Filed: Aug. 8, 2005

(65) Prior Publication Data

US 2006/0084968 A1 Apr. 20, 2006

Related U.S. Application Data

(63) Continuation-in-part of application No. 10/032,867, filed on Oct. 22, 2001, now Pat. No. 6,929,644, and a continuation-in-part of application No. 10/643,787, filed on Aug. 19, 2003, now Pat. No. 7,070,597, and a continuation-in-part of application No. 10/441,519, filed on May 20, 2003, now abandoned, and a continuation-in-part of application No. 10/351,449, filed on Jan. 22, 2003, now Pat. No. 7,112,201.

(60) Provisional application No. 60/600,419, filed on Aug. 10, 2004.

(51) Int. Cl.
*A61B 18/14* (2006.01)
*A61B 18/12* (2006.01)

(52) U.S. Cl. .......................... 606/49; 606/41
(58) Field of Classification Search .............. 606/41–49
See application file for complete search history.

(56) References Cited

U.S. PATENT DOCUMENTS 4,169,464 A 10/1979 Obrez (Continued)

FOREIGN PATENT DOCUMENTS

EP 0494732 A1 7/1992

(Continued)

OTHER PUBLICATIONS

Pacific Silk, "Designing with Silicon Synthetic Rubber" brochure, downloaded on Nov. 1, 2004.

*Primary Examiner*—Henry M Johnson, III
*Assistant Examiner*—Aaron Roane
(74) *Attorney, Agent, or Firm*—Knobbe, Martens, Olson & Bear LLP

(57) ABSTRACT

An electrosurgical instrument and method for treating varicose veins. In one embodiment, an elongate catheter has a distal working end that carries an electrosurgical energy delivery surface comprising at least one electrode with a positive temperature coefficient of resistance (PTCR) surface and/or an electrode with a pressure sensitive variable resistance to provide a smart surface for controlling Rf current flow at the interface of electrosurgical surface and the tissue. The electrode surface then can limit or modulate Rf energy delivery through the surface in response to the temperature of the surface or the engagement pressure of the surface against the engaged tissue. In operation, the smart electrosurgical surface prevents arcing at the electrode-tissue interface, and thus controls ohmic heating to prevent tissue desiccation, charring and emboli formation.

29 Claims, 4 Drawing Sheets

U.S. PATENT DOCUMENTS

| | | | |
|---|---|---|---|
| 4,232,676 A | 11/1980 | Herczog | |
| 4,492,231 A | 1/1985 | Auth | |
| 4,590,934 A | 5/1986 | Malis et al. | |
| 4,691,703 A | 9/1987 | Auth et al. | |
| 4,930,494 A | 6/1990 | Takehana et al. | |
| 4,969,885 A | 11/1990 | Farin | |
| 5,009,656 A | 4/1991 | Reimels | |
| 5,057,106 A | 10/1991 | Kasevich et al. | |
| 5,057,107 A | 10/1991 | Parins et al. | |
| 5,122,137 A | 6/1992 | Lennox | |
| 5,190,541 A | 3/1993 | Abele et al. | |
| 5,209,723 A | 5/1993 | Twardowski et al. | |
| 5,403,312 A | 4/1995 | Yates et al. | |
| 5,417,687 A | 5/1995 | Nardella et al. | |
| 5,443,463 A | 8/1995 | Stern et al. | |
| 5,451,224 A | 9/1995 | Goble et al. | |
| 5,480,397 A | 1/1996 | Eggers et al. | |
| 5,480,398 A | 1/1996 | Eggers | |
| 5,571,153 A * | 11/1996 | Wallsten | 607/98 |
| 5,593,406 A | 1/1997 | Eggers et al. | |
| 5,624,452 A | 4/1997 | Yates | |
| 5,693,051 A | 12/1997 | Schulze et al. | |
| 5,716,366 A | 2/1998 | Yates | |
| 5,776,130 A | 7/1998 | Buysse et al. | |
| 5,836,874 A | 11/1998 | Swanson et al. | |
| 5,891,142 A | 4/1999 | Eggers et al. | |
| 6,039,733 A | 3/2000 | Buysee et al. | |
| 6,113,598 A | 9/2000 | Baker | |
| 6,123,718 A * | 9/2000 | Tu et al. | 607/113 |
| 6,132,426 A | 10/2000 | Kroll | |
| 6,139,527 A | 10/2000 | Laufer | |
| 6,152,899 A | 11/2000 | Farley | |
| 6,179,832 B1 | 1/2001 | Jones | |
| 6,179,834 B1 | 1/2001 | Buysse et al. | |
| 6,277,117 B1 | 8/2001 | Tetzlaff et al. | |
| 6,298,550 B1 | 10/2001 | Kirwan, Jr. | |
| 6,352,536 B1 | 3/2002 | Buysse et al. | |
| 6,398,779 B1 | 6/2002 | Buysse et al. | |
| 6,409,725 B1 | 6/2002 | Khandkar et al. | |
| 6,429,766 B1 * | 8/2002 | Glatz-Reichenbach et al. | 338/22 R |
| 6,458,127 B1 | 10/2002 | Truckai et al. | |
| 6,527,767 B2 | 3/2003 | Wang et al. | |
| 6,533,784 B2 | 3/2003 | Truckai et al. | |
| 6,575,968 B1 | 6/2003 | Eggers et al. | |
| 6,587,731 B1 * | 7/2003 | Ingle et al. | 607/101 |
| 6,673,042 B1 * | 1/2004 | Samson et al. | 604/104 |
| 2003/0018327 A1 | 1/2003 | Truckai et al. | |
| 2003/0078577 A1 | 4/2003 | Truckai et al. | |
| 2003/0078578 A1 | 4/2003 | Truckai et al. | |
| 2003/0139741 A1 | 7/2003 | Goble et al. | |
| 2003/0144652 A1 | 7/2003 | Baker et al. | |
| 2003/0171748 A1 | 9/2003 | Truckai et al. | |
| 2003/0216732 A1 | 11/2003 | Truckai et al. | |
| 2004/0215185 A1 | 10/2004 | Truckai et al. | |

FOREIGN PATENT DOCUMENTS

| | | |
|---|---|---|
| EP | 518230 A 1 | 5/1996 |
| FR | 2647683 A1 | 12/1990 |
| GB | 2037167 A | 7/1980 |
| WO | WO 94/24949 | 11/1994 |
| WO | WO 94/24951 | 11/1994 |
| WO | WO 2005/046779 A2 | 5/2005 |

* cited by examiner

ELECTROSURGICAL INSTRUMENT AND METHOD

CROSS-REFERENCE TO RELATED APPLICATIONS

This application claims benefit of Provisional U.S. Patent Application Ser. No. 60/600,419 filed Aug. 10, 2004 titled Electrosurgical Instrument and Method for Treatment of Varicose Veins. This application is a continuation-in-part of U.S. patent application Ser. No. 10/032,867 filed Oct. 22, 2001 issued as U.S. Pat. No. 6,929,644; and is a continuation-in-part of U.S. patent application Ser. No. 10/351,449 filed Jan. 22, 2003 issued as U.S. Pat. No. 7,112,201; and is a continuation-in-part of U.S. patent application Ser. No. 10/441,519 filed May 20, 2002 now abandoned; and is a continuation-in-part of U.S. patent application Ser. No. 10/643,787 filed Aug. 19, 2003 issued as U.S. Pat. No. 7,070,597. All of the above applications are incorporated herein by this reference and made a part of this specification.

BACKGROUND OF THE INVENTION

1. Field of the Invention

This invention pertains to methods and devices for endovascular surgery, and more particularly to devices and methods for treating varicose veins.

2. Description of the Related Art

Varicose veins are distended, visible superficial veins on the legs, and are almost always the result of problems with valves within the venous system of the leg. All leg veins contain one-way flap valves which are designed to help the flow of blood in the veins in an upward direction on its return to the heart. When one or more of these valves fails to function correctly and leaks, some blood is able to flow back down into the leg in the wrong direction and tends to distend branches of superficial veins under the skin. Over a period of time, this additional pressure of blood causes the veins to stretch, bulge and become visible. At the same time, tiny capillary branches of the veins are also overfilled with blood, producing multiple spider veins and often a purple discoloration. Leaky venous valves can occur at any site in the leg but the great majority of varicose veins are caused by faulty valves in the groin or behind the knee. At both these sites there is a major junction at which superficial veins (those subject to varicose veins) flow into the important deep veins of the leg, with a one-way valve to control flow at the junction. Numerous surgical treatments of varicose veins have been developed such surgical stripping and surgical vein removal. Also, radiofrequency (Rf) ablation catheters and laser catheters are used to shrink and ablate varicose veins.

SUMMARY OF THE INVENTION

In general, the apparatus of the invention comprises a catheter member with a working end having an electrosurgical energy delivery surface for translating along a vessel lumen to shrink and occlude the lumen. The working end comprises a resilient polymer sleeve that is moveable from a first reduced cross-section for introduction to a second expanded cross-section for engaging the vessel wall. In one embodiment, the working end is a resilient sleeve of a polymer having a memory expanded shape that is dimensioned to slide over a guidewire wherein the guidewire is capable of acting as a substantially rigid member to maintain the sleeve in a linear pre-deployed configuration.

Of particular interest, the working end of the sleeve has exposed electrodes that have a PTCR (positive temperature coefficient of resistance) coating that can modulate Rf current flow to the vessel lumen without thermocouples and controller feedback circuitry. The PTCR material consists of a conductively doped polymer such as silicone. The electrodes are embedded in the catheter sleeve and can operate in bi-polar or mono-polar mode. The PTCR material maintains a low base resistance over a selected temperature range with a dramatically increasing resistance above a selected narrow temperature range as Rf energy is delivered to tissue through the PTCR material. In operation, it can be understood that current flow through the PTCR material will apply active Rf energy (ohmic heating) to the engaged tissue until the point in time that any portion of the material is heated to a range that substantially reduces its conductance. This effect will occur across the PTCR surface thus allowing portions thereof to deliver an independent level of power therethrough. This localized limiting of Rf current can be relied on to prevent any arcing in or about the electrosurgical surface. The system thus eliminates the possibility of tissue char and the potential of emboli. Further, when the PTCR material is elevated in temperature to the selected thermal treatment range, the retained heat of the material volume can also apply thermal energy to the engaged vessel lumen. In one embodiment, the working end will modulate the application of energy to the vessel wall between active Rf ohmic heating and passive conductive heating to maintain a selected temperature level to shrink and occlude the vessel.

DETAILED DESCRIPTION OF THE INVENTION

Figure 1:
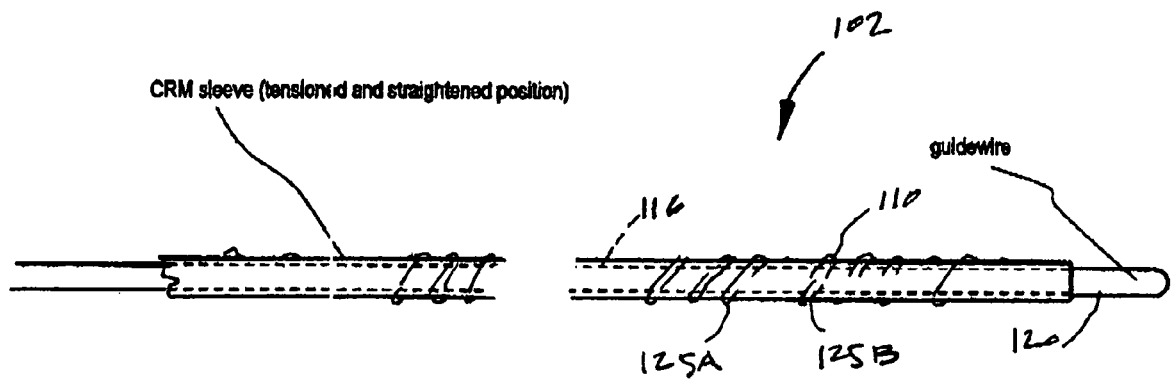
FIG. 1 is a side view of the distal end of a Type "A" catheter-like sleeve and guidewire of the invention in a first linear shape for endoluminal navigation.
Figure 2:
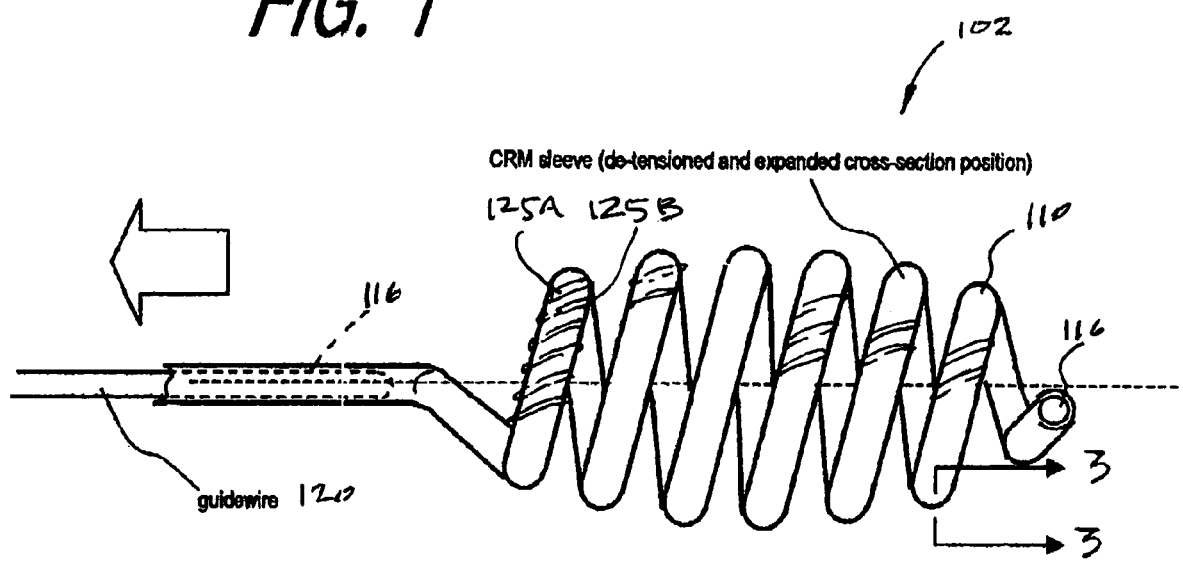
FIG. 2 is a side view of the Type "A" catheter sleeve of FIG. 1 with the guidewire withdrawn and the sleeve in a second expanded shape for treating a varicose vein.

1. Catheter sleeve including PTCR electrosurgical surface for treating varicose veins. FIGS. 1 and 2 illustrate the distal working end 102 of a Type "A" elongated catheter that includes a distal region that includes a distal sleeve end 110 that comprises an electrosurgical surface 112 corresponding to the invention that is adapted for controllably applying energy to the lumen of a blood vessel or other tubular body structure. The sleeve 110 can be any suitable length along axis 115 for endoluminal navigation to a targeted site. The cross-section of the sleeve can be a suitable dimension, for example, 4 French with a 2 French lumen indicated at 116. The lumen 116 is dimensioned to slide over a guidewire 120 with the guidewire capable of acting as a substantially rigid member to straighten the sleeve 110 to allow endoluminal navigation.

Figure 3:
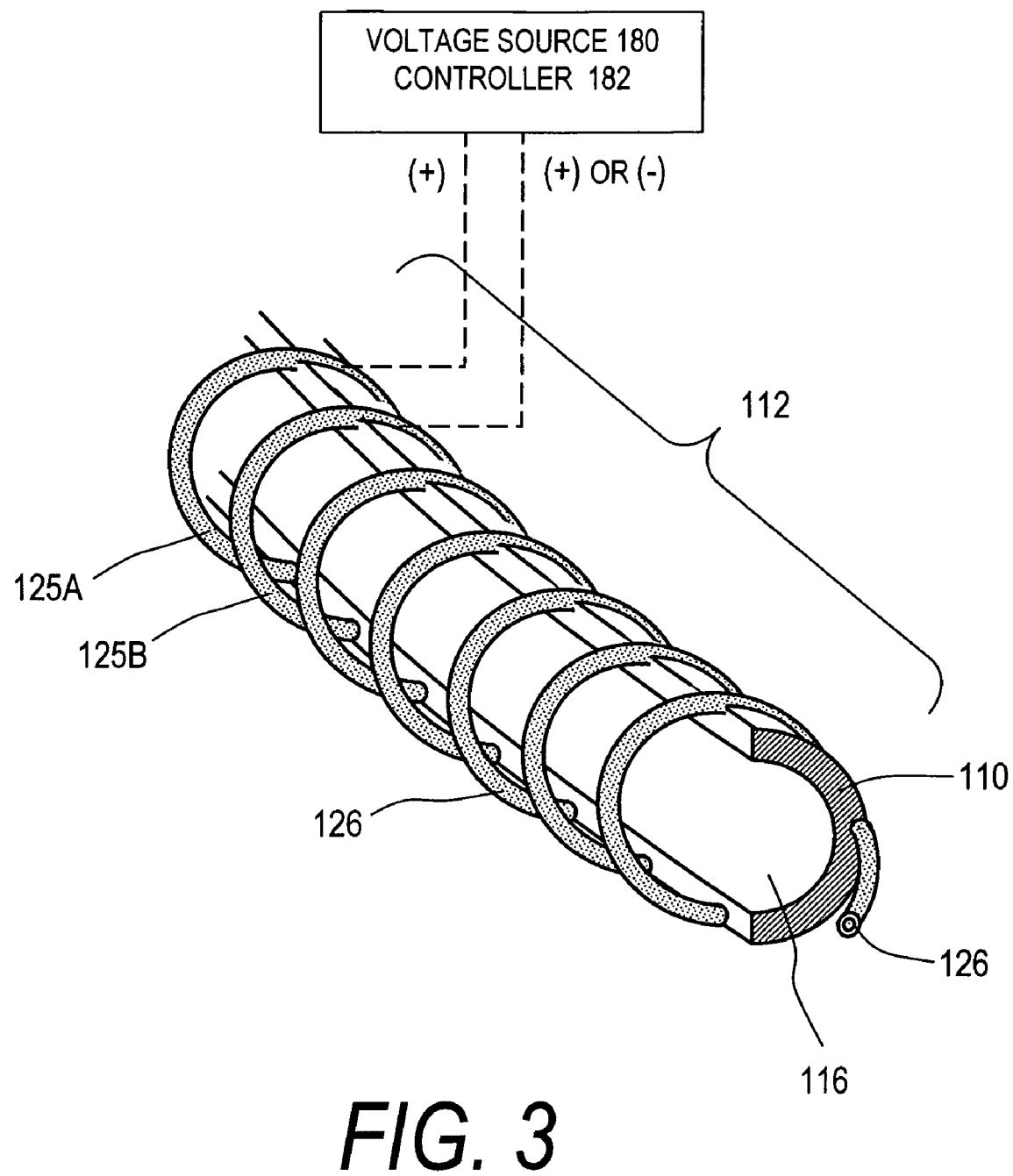
FIG. 3 is a cut-away view of a small portion of the Type "A" sleeve of FIG. 1 taken along line 3-3 of FIG. 2.

In the exemplary embodiment of FIGS. 1 and 2, it can be seen that sleeve 110 has a first untensioned condition in FIG. 2 that has an expanded cross-sectional shape for engaging the walls of a vessel lumen. In FIG. 1, the sleeve 110 is in a second tensioned linear condition with a lesser cross-section when the guidewire 120 extends therethrough as in FIG. 1. The untensioned, expanded cross-sectional shape of the sleeve 110 in FIG. 2 is provided by the memory shape of the polymer of the sleeve, and/or by at least one resilient spring element (not shown) molded into the wall 122 of sleeve 110. Preferably, as can be seen in FIG. 3, electrode elements 125A and 125B in sleeve wall 122 can also provide resilient spring properties to maintain a thin sleeve 110 in an open condition. In use, the working end 102 of sleeve 110 is navigated to the targeted site in the tensioned, linear configuration of FIG. 1. Thereafter, the guidewire is withdrawn partly (see FIG. 2) to allow the sleeve 110 to expand to its untensioned position as in FIG. 2.

The sleeve 110 is fabricated of a suitable polymer such as a silicone that is easily deformable between its linear and expanded cross-sectional shapes (FIGS. 1 and 2) after release from its constraint by the guidewire 120. It should be appreciated that the sleeve member 110 also can be a rod-like member and constrained by, and released from, a bore in a more rigid catheter (not shown). The expanded cross-section of sleeve 110 in FIG. 2 can define an outer diameter of any dimension, for example 2 mm. to 2 cm. and will thus gently push outward to engage the vessel wall as the working end is pulled along the vessel lumen.

In one embodiment, the sleeve 110 provides a distal working end including an electrosurgical energy delivery surface 112 that comprises helical windings or conductors 125A and 125B that function as mono-polar or bi-polar electrodes wherein the conductors 125A and 125B have a surface coating of a positive temperature coefficient of resistance (PTCR) polymeric material 126 that functions to control and limit Rf current flows and ohmic heating in the engaged tissue. In the exemplary embodiment of FIG. 1, shown in cut-away views in FIGS. 3 and 4, it can be seen that the conductors or electrodes 125A and 125B are coupled to, but exposed, in a surface of sleeve wall 122 which is fabricated of a non-conductive polymer. The polymeric PTCR material 126 thus is exposed to provide the electrosurgical energy delivery surface 112 that is adapted to interface with the vessel lumen. More in particular, the PTCR material comprises a non-conductive polymer that is doped with conductive particles. Suitable PTCR materials corresponding to the invention are described in co-pending U.S. patent applications listed in the Section above titled CROSS-REFERENCE TO RELATED APPLICATIONS. The polymer portion of the PTCR material can have any thermal conductivity property, but preferably has a low thermal conductivity. The conductive particles can be carbon, gold, platinum, silver, or a stainless steel coated with gold, platinum, silver or the like. In one embodiment, the ration by weight of the polymer-to-conductive particles can range from about 10/90 to about 70/30 (polymer/carbon particles) to provide the selected range at which the sleeve wall will function to substantially limit electrical conductance therethrough at a selected switching range between about 80° C. and 120° C. The non-conductive base polymer 160a can comprise silicone, high density polyethylene or polypropylene.

Figure 4:
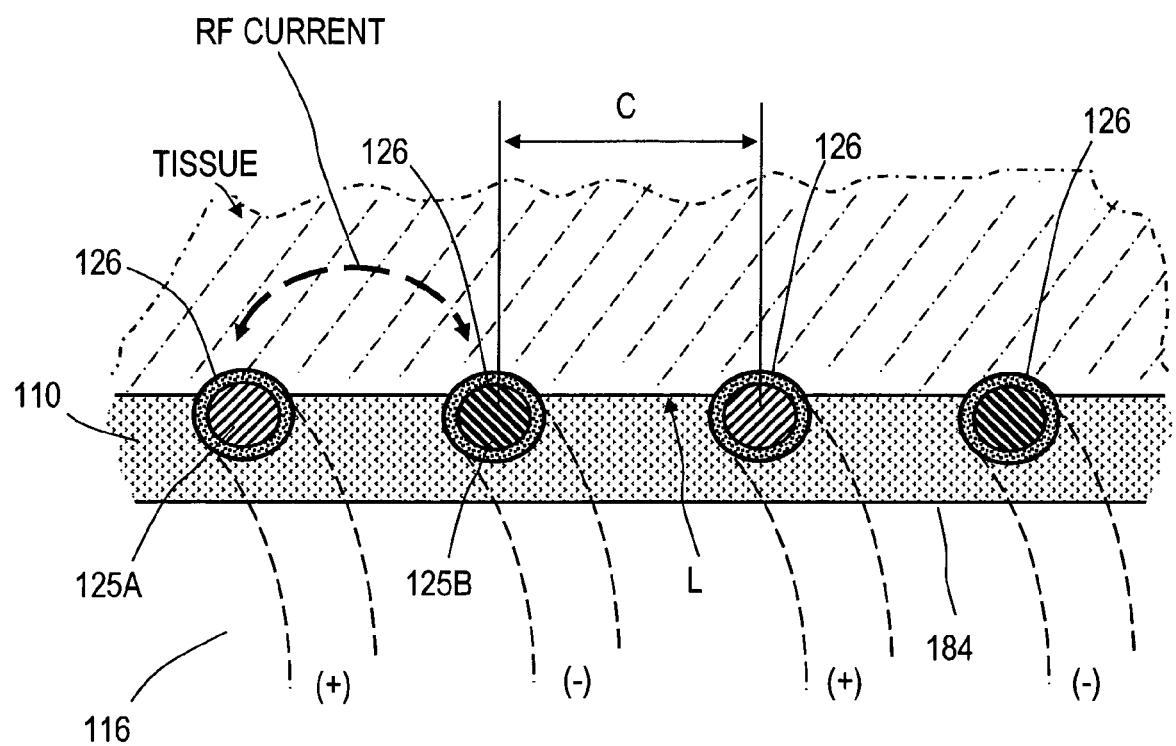
FIG. 4 is a sectional view of the Type "A" sleeve of FIGS. 1-2 engaging tissue.

As can be seen in FIGS. 3 and 4, the polymer of sleeve wall 122 can be formed partly around the conductive elements or electrodes 125A and 125B and maintain a selected spacing therebetween. The conductive elements 125A and 125B are coupled to a voltage (Rf) source 180 and controller 182 by a connector cable that is detachable from a proximal handle end of sleeve 110. Thus, the Rf source 180 can apply electrical potential of a first and second polarities (+) and (−) to the conductors 125A and 125B and PTCR surfaces 126 and thereafter to the engaged vessel lumen L.

In the embodiment of FIG. 3, the conductive elements 125A and 125B comprise spaced apart helical coils that are indicated as having opposing polarities, or the conductors 125A and/or 125B can have a common polarity to allow operation in a mono-polar manner in cooperation with a ground pad 185. In one embodiment, the voltage source 180 and controller 182 are configured to switch energy delivery by means of a multiplexer between bi-polar and mono-polar modes. As also can be seen in FIG. 3, the inner wall surface 184 of wall 122 comprises a portion of the insulative material of sleeve wall 122 that prevents any contact of the electrical components of the sleeve (i.e., PTCR material and electrodes 125A and 125B) with the guidewire 120 or blood in the sleeve's lumen during operation (see FIGS. 1-2).

Figure 5:
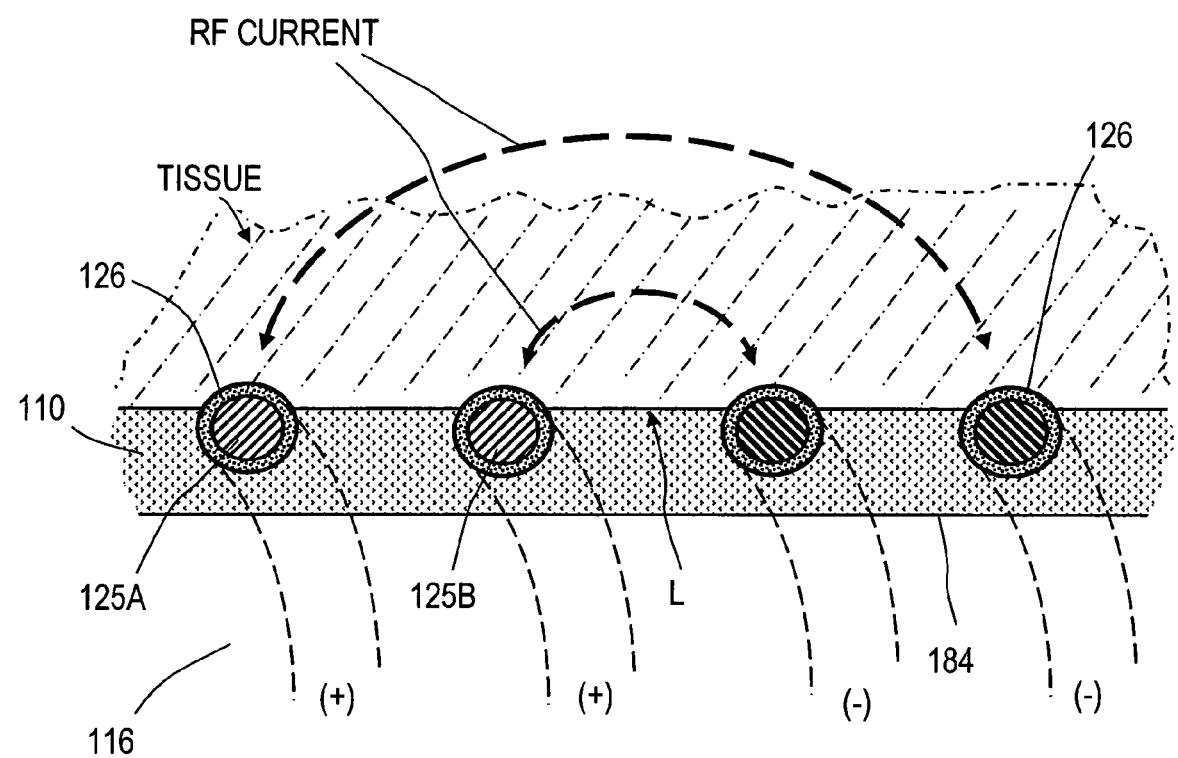
FIG. 5 is a sectional view of the Type "B" sleeve similar to that of FIG. 4.

In one method of the invention, the sleeve 110 and electrosurgical surface 112 can limit current flows in tissue and modulate the delivery of energy through electrosurgical surface 112 to the vessel lumen L (see FIGS. 4 and 5). The distal end of the sleeve 110 is advanced distally through a targeted varicose vein. The working end is then expanded (see FIG. 2) and energized as it is pulled retrograde through the vein. Rf energy application to the vessel lumen will shrink and damage the vessel wall to thereby occlude the vein. When operating in a mono-polar mode as described above, the PTCR material 126 illustrated in FIGS. 3 and 4 will cause current flow in the engaged tissue until the vessel wall reaches a selected switching temperature and thereafter heat is conducted back from the tissue to the PTCR material 126. Local regions of the PTCR material will then switch off Rf current delivery therethrough which will prevent arcing, charring and tissue desiccation at the interface of the electrosurgical surface 112 and the tissue. This effect will about the surface of each electrode to provide spatially localized modulation of ohmic heating in the engaged tissue. The PTCR material 126 thus senses the tissue temperature that results from ohmic heating and limits current flows to maintain the temperature of the engaged tissue at or about the targeted treatment range.

Referring again to FIG. 4, the conductive elements 125A and 125B are shown operating in a bi-polar mode and wherein the current flows in tissue a selected distance C (not-to-scale; electrode center-to-center dimension) which in turn controls the depth of ohmic heating in tissue. The electrosurgical surface delivers Rf current flows to the endoluminal tissue wherein the Rf current flows are limited by changes in temperature in at least portions of the PTCR material 126 resulting in the denaturing of proteins within the engaged tissue while substantially preventing desiccation and charring of the tissue. The protein denaturation causes tissue effects that include shrinkage, ablation, occlusion and vessel closure. The sleeve 110 assembly can be manufactured in a number of manners such as extruding an inner portion of the insulative sleeve 110 then using precision windings systems to wind at least one coil of fine wire (with PTCR coating) about the inner sleeve portion. Thereafter, and additional polymeric material can be deposited to partly embed the PTCR coated coils in the sleeve surface. The spacing of the electrodes 125A and 125B and temperature resistance profile of the PTCR material 126 are selected to cause the desired Rf current depth and switching temperature.

In another mode of operation, still referring to FIG. 4, electrical potential of opposing polarities is applied between conductors 125A and 125B which results in current flow through the PTCR material 126 and the engaged tissue T—depending on center-to-center spacing and the conductivity of the PTCR material 126 which is in constant flux as its temperature changes from its conductive heating from engaged ohmically heated tissue. By this means, as described above, the surface 112 acts as a continuously localized temperature control mechanism without the thermocouples and feedback circuitry that are common in many prior art electrosurgical devices. The entire working end assembly can be pulled proximally within the lumen of the blood vessel to cause ohmic heating of a selected length of the blood vessel. The PTCR material 126 will prevent any blood from coagulating about the surface 112 due to its ability to prevent hot-spots or charring as described in previous disclosures referenced above. The method as described above will shrink and occlude the blood vessel to thereby treat varicose veins.

FIG. 5 illustrates the distal working end of another embodiment of sleeve and electrosurgical surface 112 that is substantially the same as the previously described embodiment. This system is provided with a controller 182 that allows selection of the center-to-center distance between groups of two or more helical conductors operating in a bi-polar mode, in addition to singly paired electrodes as shown in FIG. 4. The system also can be provided with a multiplexer to automatically switch between different single and multiple arrangements of electrode windings. In this embodiment, at least 4 separate helical coils, or as many as about 24 coils, are independently connected to the electrical source and controller. In operation, the progressively more widely spaced apart bi-polar electrode groups can cause ohmic heating to a greater selected depth in the engaged tissue. Thus, a single diameter sleeve 110 can be adapted for optimal ohmic heating depth no matter the diameter and wall thickness of the blood vessel, whether the blood vessel in 2 mm. or 10 mm.

In another embodiment, the sleeve can be similar in all respects to the embodiments of FIGS. 1-5 except that the coating on the electrodes can be a pressure sensitive resistive material as disclosed in 10/032,867 filed Oct. 22, 2001; and U.S. patent application Ser. No. 10/351,449 filed Jan. 22, 2003; and U.S. patent application Ser. No. 10/441,519 filed May 20, 2002.

It should be appreciated that the scope of the invention includes any catheter sleeve 110 that is adapted to provide a first contracted shape for endoluminal navigation and a second expanded shape for engaging the vessel walls, wherein the electrosurgical surface 112 of the sleeve includes at least one electrode and a PTCR polymer 126 having a positive temperature coefficient of resistance. For example, the member be articulatable with pull-wires or the like, or the member may have a core of a shape memory material such as a Nitinol wire or tube.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A catheter comprising an elongate flexible member configured for endoluminal navigation with a working end having an electrosurgical surface including a material having a positive temperature coefficient of resistance (PTCR), and an electrical source operatively coupled to the electrosurgical surface;

wherein the working end of the flexible elongate member comprises a tubular member defining an internal lumen;

wherein the tubular member is moveable between a first, non-expanded, configuration in which the tubular member is generally straight and the internal lumen extends along a longitudinal axis of the catheter, and a second, expanded configuration in which the tubular member forms a helix such that the internal lumen does not extend along the longitudinal axis but is instead coiled around it;

wherein the PTCR material of the electrosurgical surface is configured for direct contact with bodily tissue wherein the PTCR material is adapted to transmit electrical energy directly to bodily tissue.

2. The catheter of claim 1 wherein the PTCR material overlies at least one electrode.

3. The catheter of claim 1 wherein the PTCR material overlies spaced apart opposing polarity electrodes.

4. The catheter of claim 3 further comprising a multiplexer operatively coupled to the opposing polarity electrodes and the electrical source.

5. The catheter of claim 1 wherein the working end includes a shape memory alloy component for providing the second, expanded configuration.

6. The catheter of claim 1, wherein the working end is more tensioned in the first, non-expanded configuration than in the second, expanded configuration.

7. The catheter of claim 6, wherein the working end is in repose in the second, expanded configuration.

8. The catheter of claim 1, further comprising a straightening member received in the tubular member, wherein the tubular member expands to the second, expanded configuration when the straightening member is retracted from the tubular member.

9. The catheter of claim 8, wherein the tubular member comprises a shape memory alloy.

10. The catheter of claim 1, wherein the electrosurgical surface further comprises helical electrodes that wind around the working end.

11. The catheter of claim 10, wherein the helical electrodes comprise first and second helical electrodes configured for operation in opposing polarity.

12. The catheter of claim 11, wherein the first and second helical electrodes are wound in a parallel nonintersecting configuration around the elongate member.

13. The catheter of claim 12, wherein the first and second helical electrodes alternate along the length of the elongate member.

14. The catheter of claim 10, wherein the helical electrodes have spring properties sufficient to cause the working end to attain the second, expanded configuration when unconstrained.

15. The catheter of claim 1, wherein the electrosurgical surface comprises at least one electrode arranged helically around said tubular member when said tubular member is in said second, expanded configuration.

16. The catheter of claim 1, wherein the PTCR material is polymeric.

17. The catheter of claim 1, wherein PTCR material of the electrosurgical surface is configured to engage with vein wall tissue when deployed in a vein.

18. A catheter comprising an elongate flexible member configured for endoluminal navigation with a working end having an electrosurgical surface comprising an electrode with a coating of a polymeric material having a positive temperature coefficient of resistance (PTCR);

wherein the working end of the flexible elongate member comprises a tubular member defining an internal lumen;

wherein the tubular member is moveable between a first, non-expanded, configuration in which the tubular member is generally straight and the internal lumen extends along a longitudinal axis of the catheter, and a second, expanded configuration in which the tubular member forms a helix such that the internal lumen does not extend along the longitudinal axis but is instead coiled around it;
wherein the PTCR material of the electrosurgical surface is configured for direct contact with bodily tissue wherein the PTCR material is adapted to transmit electrical energy directly to bodily tissue.

19. The catheter of claim 18 wherein the electrosurgical surface comprises opposing polarity electrodes with coatings of a polymeric material having a PTCR.

20. The catheter of claim 19, wherein the opposing polarity electrodes are helical electrodes that wind around the working end.

21. The catheter of claim 20, wherein the helical electrodes have spring properties sufficient to cause the working end to attain the second, expanded configuration when unconstrained.

22. The catheter of claim 19, wherein the opposing polarity electrodes are first and second helical electrodes wound around the elongate member such that the first and second electrodes alternate along the length of the elongate member.

23. The catheter of claim 18, wherein the working end is more tensioned in the first, non-expanded configuration than in the second, expanded configuration.

24. The catheter of claim 23, wherein the working end is in repose in the second, expanded configuration.

25. The catheter of claim 18, further comprising a straightening member received in the tubular member, wherein the tubular member expands to the second, expanded configuration when the straightening member is retracted from the tubular member.

26. The catheter of claim 25, wherein the tubular member is a shape memory alloy.

27. The catheter of claim 18, wherein the electrode is arranged helically around said tubular member in at least one of said first and second configuration.

28. The catheter of claim 18, wherein the PTCR material of the electrosurgical surface is configured to engage with vein wall tissue when deployed in a vein.

29. The catheter of claim 18, wherein the wherein the PTCR material of the electrosurgical surface is configured for helical apposition to the vein wall.

* * * * *